United States Patent [19]

Thiele et al.

[11] Patent Number: 4,781,836

[45] Date of Patent: Nov. 1, 1988

[54] METHOD FOR BIOMETHANATION

[75] Inventors: Jurgen Thiele, East Lansing; Joseph G. Zeikus, Okemos, both of Mich.

[73] Assignee: Michigan Biotechnology Institute, East Lansing, Mich.

[21] Appl. No.: 863,977

[22] Filed: May 16, 1986

[51] Int. Cl.⁴ .......................... C02F 3/28; C02F 11/04; C12P 5/02
[52] U.S. Cl. .................. 210/603; 210/630; 210/683; 210/670; 435/167; 48/197 A
[58] Field of Search .............. 210/603, 631, 670, 683, 210/692; 435/167, 801; 48/197 A

[56] References Cited

U.S. PATENT DOCUMENTS

| | | | |
|---|---|---|---|
| 4,134,830 | 1/1979 | Skogman et al. | 210/603 |
| 4,659,471 | 4/1987 | Molin et al. | 210/603 |
| 4,696,746 | 9/1987 | Ghosh et al. | 210/603 |
| 4,722,741 | 2/1988 | Hayes et al. | 210/603 |
| 4,735,723 | 4/1988 | Mulder | 210/603 |

*Primary Examiner*—Benoit Castel
*Attorney, Agent, or Firm*—Quarles & Brady

[57] ABSTRACT

An improved process for the biomethanation of an organic substrate includes treating the substrate in a first reactor to form organic acid anions, passing an aqueous preparation containing dissolved organic anions through an anion exchanger so that the organic acid anions are adsorbed and separated from the remainder of the aqueous preparation, desorbing the organic acid anions and passing the desorbed acids to a second reactor containing methanogenic bacteria which convert the acids to methane. In a preferred embodiment, a bicarbonate solution is produced in the second reactor and it is used to desorb the organic acid anions and regenerate the anion exchanger into the bicarbonate form.

11 Claims, 1 Drawing Sheet

METHOD FOR BIOMETHANATION

FIELD OF THE INVENTION

The present invention relates to the microbial biomethanation of organic substrates. More particularly, it relates to an improved anaerobic microbial biomethanation process for the production of methane from organic materials and an apparatus for performing the method.

BACKGROUND OF THE INVENTION

Biomethanation is a process by which organic matter is decomposed by the simultaneous action of mixed microbial consortia to form methane and carbon dioxide. The microorganisms in these consortia can be classified into three major trophic groups, namely:

I. hydrolytic fermentative bacteria;
II. syntrophic $H_2$-producing acetogenic bacteria;
III. $H_2$ and acetate consuming methanogenic bacteria.

The hydrolytic fermentative bacteria of group I can convert a complex organic biomass into simple organic fermentation products including ethanol and organic acids, which are also referred to as volatile fatty acids (VFA's), such as formate, acetate, lactate, propionate, butyrate and benzoate, and hydrogen ($H_2$) and carbon dioxide ($CO_2$) gases. The syntrophic $H_2$ producing bacteria of group II further degrade the organic acids and alcohol into the methanogenic precursors acetate and $H_2$, and the methanogenic bacteria of group III form methane and carbon dioxide via acetate-cleavage and consume $H_2$ by reduction of $CO_2$ to methane.

These trophic groups constitute a complete microbial food chain and they perform some unique functions like the interspecies $H_2$-transfer process. The interspecies $H_2$-transfer process in a biomethanation-ecosystem is an essential ecophysiological interaction between the $H_2$-producing acetogenic bacteria (trophic group II) and $H_2$-consuming methanogenic bacteria (trophic group III), where $H_2$ is an intermediate produced by the trophic group II and it is consumed by trophic group III. $H_2$ even at very low concentrations inhibits metabolism of trophic group II. Thus, the simultaneous $H_2$-consuming activity of methanogenic bacteria in the biomethanation ecosystem (trophic group III) must maintain $H_2$-partial pressures low enough to allow growth and metabolism of trophic group II by a so called "syntrophic growth".

Biomethanation has been used in waste treatment to get rid of organic waste.

Prior art anaerobic waste treatment systems (anaerobic contact digestors) used a non-engineered complex microbial ecosystem for waste biomethanation that achieves efficient biological oxygen demand (BOD) removal under anaerobic conditions with methane as a byproduct. However, slow growth of the involved microflora and poor methane productivities make it impossible to operate anaerobic waste treatment plants close to the theoretical biological limits of the ecosystems. Resulting large digestor volumes with high investment costs limit the economic applicability of the technology to high volume waste streams.

The so called "advanced reactor concepts'" improve the methane productivities by either recycling of the active bacterial biomass into the process (sludge recycle) and/or the attachment of the active microbial flora to support materials (anaerobic filters). A two stage treatment system where the microbial ecosystem is separated into two populations contained in two different reactors connected by a common liquid phase and operated at acidic pH-values (acidogenic stage) and neutral pH-values (methanogenic stage) has been proposed to improve biomethanation rates. However, the desired methane ($CH_4$) productivities are rarely obtained. The prior art two stage biomethanation processes do not appear practical because they require high capital costs and two different stages. Upflow-anaerobic-sludge-blanket reactors (UASB-reactors) can render possible high methane productivities because the different microbial trophic groups are associated in discrete microbial granules. However, this system is not used widely because of process instabilities caused by toxic substrate, substrate overloading, nutrient inadequacy and unknown factors which disrupt granulation.

The previously described "advanced reactor concepts" do not involve a microbiological improvement of ecophysiological interactions during the process of biomethanation. The potentially great improvements in biomethanation processes that can be achieved by eco-engineering the physiology of the biocatalysts (i.e. creating the optimum environment for the mixed biocatalyst) is prohibited by present reactor concepts. In prior art processes all the trophic groups are either all placed in one reactor (fixed bed or granules) or in two separate reactors linked by a common liquid phase; the common liquid phase restricts the possibility for either selective improvements in a single reaction step or microbial interactions because the liquid phase is in contact with all the different trophic groups.

BRIEF SUMMARY OF THE INVENTION

The object of the present invention is to disclose an improved biomethanation process which can be used with a broad spectrum of waste substrates, and which enhances the specific volumetric reaction rates for the biomethanation of organic matter, and removes toxicants inhibitory to biomethanation.

The biomethanation process of the present invention is a multiple stage or step process which utilizes an apparatus comprised of two independent reactors linked by at least one anion exchanger that functions to concentrate a carbon source, such as organic acids and alcohols, from the first reactor for use in the second reactor where the carbon source is converted to methane. The anion exchanger also separates undesired toxicants from the carbon source that could interfere with the second stage of the process.

In the apparatus used in the present inventive process there is no direct or common liquid interface between the two reactors. The use of a first independent reactor for the hydrolytic process and a second independent reactor for the syntrophic and methanogenic processes permits optimal independent process design for the independent reactors in all the following respects:
 temperature
 pressure
 pH
 support materials
 medium composition
 microbial composition
 essential nutrient requirements
 individual dilution rates Thus, the process of the present invention overcomes the key weaknesses of the prior art processes namely, process instability and low methane productivity.

We have discovered that the best point for a stage separation in a biomethanation process involving complex microbial food chains is the carbon transfer between the trophic groups I and II. Therefore, in the process of the present invention, the food chain is separated into an acidogenic stage in the first complex organic hydrolysis reactor (COHR) and a methanogenesis stage in the second syntrophic-biomethanation reactor (SBR). The first and second reactors are connected by the anion exchanger(s); however, there is no common liquid phase connecting the reactors.

The process takes advantage of the common properties and nutritional needs of trophic group II and III and the basic imcompatibility of these trophic groups with the properties and needs of organisms of trophic groups I (optimum pH-range, doubling times, anaerobiosis, essential nutrients). It further provides the essential prerequisite for an interspecies $H_2$ transfer by including $H_2$-producing acetogenic bacteria and methanogenic bacteria in the same second reactor (SBR) in form of a microbial aggregate.

The reaction products of the first stage and the first reactor are either anions of organic acids (formate, acetate, lactate, propionate, butyrate and benzoate) or alcohols which are converted into such anions by consecutive reactions. The major soluble endproduct of the concerted action of the trophic groups II and III in the methanogenic stage is bicarbonate (Table 1). So anion-exchangers can be used to provide a substrate shuttle probess employing the bicarbonate thus produced to desorb the organic acid and to recharge the anion exchanger.

In the preferred process, the fermentation product from the hydrolysis stage in the first reactor is first filtered to separate the solid phase from the liquid phase and the liquid phase containing the dissolved acid anions is passed over an anion-exchange material presented in the bicarbonateform. The anion-exchange material has a greater selectivity for bicarbonate than for the organic acid anions. The pH-value of the fermentation broth is loW (pH=5-6), therefore, the bicarbonate ions, which dissociate from the anion-exchanger, are protonated and partly disintegrate into $CO_2$ and $H_2O$. As a consequence of this, the dissolved organic acid anions bind to the anion-exchange-material and are removed from the rest of the liquid phase. The residue of the liquid phase is either discarded or recycle to the first reactor.

The separated solid phase includes microbial cells, cell aggregates, organic or inorganic support materials, on the surface of which the microbial cells are attached and organic particulate carbon substrates. It can be used as an animal feed, biocatalyst or starter culture source or recycled to the first reactor.

In the second reactor there is a dense particulate syntrophic and acetoclastic consortium comprising aggregates of microorganisms belonging to the trophic groups II and III, which are either attached to themselves or to particles and which preferably have a buoyant density of greater than 1.05 g/cm$^3$. The consortium can be prepared by treating sludge from a prior biomethanation process in a continuously operating upflow reactor with a near neutral growth medium (e.g. PBB) containing essential minerals, a low concentration of inorganic phosphates and sulfides and at least 5 m Mol/l each of at least three of the organic acids to be converted at an increasing feed rate. The microorganisms in the second syntrophic methanogenic reactor convert the organic acid anions to $CH_4$, $CO_2$, and $HCO_3^-$ at essentially neutral pH-values (pH=6.6-7.8). Thus, the liquid phase in the second reactor contains high concentrations of dissolved $HCO_3^-$, typically 50-100 mM.

As previously indicated the selectivity of the anion-exchange material is higher for bicarbonate than for the organic acid anions and the organic acid anions are replaced from the anion-exchange material by the addition of bicarbonate. The aqueous liquid product from the second reactor is the preferred source of the bicarbonate solution which can be passed through the anion-exchange material.

In the anion exchanger process, some of the bicarbonate solution also is removed from the second methanogenesis reactor and introduced into the hydrolysis stage in the first reactor. Thus, the process provides at the same time base for the hydrolysis stage in the first reactor and acid for the second reactor because carbonic acid is a weaker acid than the organic acid biomethanation substrates. This also maintains a stable pH-difference between both reactors.

A very important property of the anion-exchange substrate shuttle process is shown in Table 2. Due to the law of mass and charge conservation, an electroneutral anion substrate shuttle system improves the $CH_4$-content of the produced biogas because for each mole organic acid converted, one mole of bicarbonate is removed from the methanogenesis stage. Since acetate and propionate are the dominant organic acids in biomethanation processes, methane contents greater than 90% can be realized with the proposed anion-exchange substrate shuttle system (Table 2). Thus, the process increases the potential economic value of the produced gas by separating the two gases which upgrades the Btu content of the methane gas and produces a separate clean $CO_2$ gas.

DESCRIPTION OF PREFERRED EMBODIMENT

Figure 1:
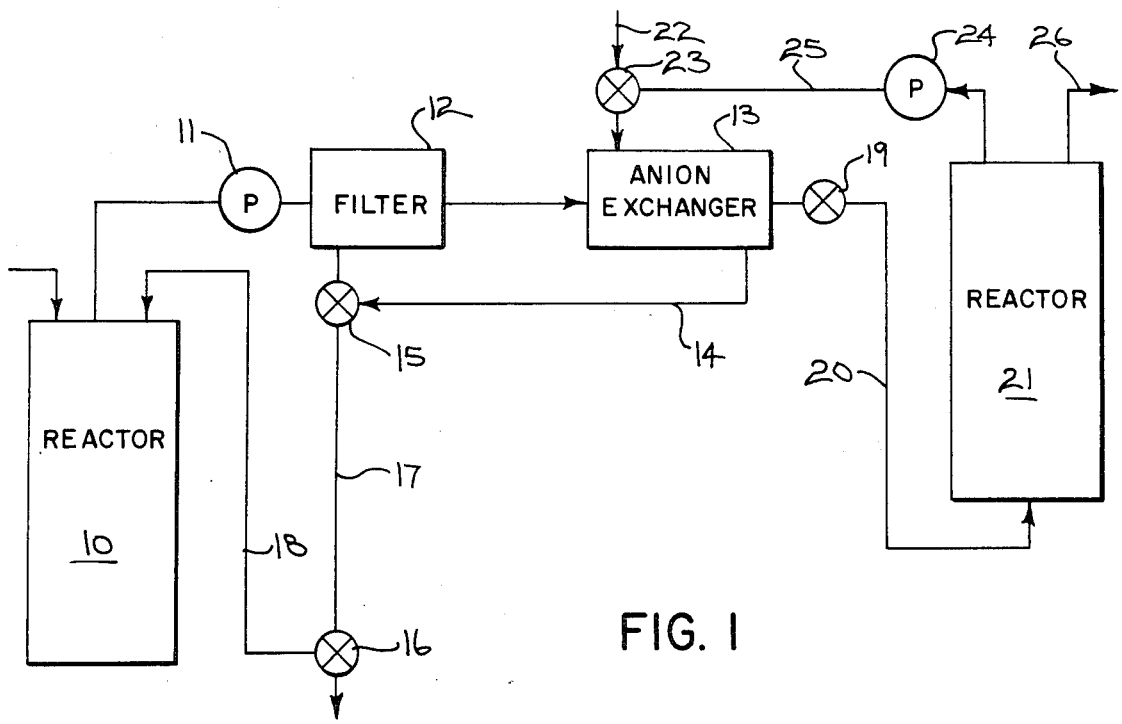
FIG. 1 is a schematic view of the preferred apparatus of the present invention for a batch process; and, FIG. 2 is a schematic view of the preferred apparatus for a continuous process.

The preferred embodiment of the invention will be described in connection with the drawing in which the solid lines represent tubing. The apparatus of FIG. 1 which is for use in a batch process includes a first reactor 10 for the complex organic hydrolysis. It may be of any suitable type and it is operated at a pH of 5.5-6.5 to produce an organic acid anion rich liquid, which is pumped via pump 11 through tubing to a filter 12 which has the ability to separate the solid phase consisting of suspended material, including cells from the liquid phase. The filter 12 is preferably a membrane filter.

The filtrate containing theorganic acid anions is then passed over anion exchange material in an anion-exchanger 13, which is provided in the bicarbonate form, to adsorb the organic acid anions and leave a liquid of neutral pH, which is essentially free of organic acids and rich in bicarbonate. The thus obtained liquid is then either recycled into the hydrolysis reactor 10 via tubing 14, valves 15 and 16 and tubing 17, 18 for pH control or it can be released into the environment as a treated waste via tubing 14, 17 and valves 15 and 16.

The filtration step also produces a solid phase or paste rich in cells from the fermentation product of the first organic hydrolysis reactor 10; the solid phase can either be recycled into the first reactor 10 via tubing 17 and 18 and valves 15 and 16 to increase the concentration of active biomass or removed from the apparatus via tubing 17 and valves 15 and 16 to be used as animal feed, a starter culture or a biocatalyst for further biotechnological conversions.

The organic fatty acid anions on the anion exchange material in the exchanger 13 can be desorbed with bicarbonate solution and the desorbed acids transported via valve 19 and tubing 20 to the second reactor 21 where they are converted by the methanogenic microorganisms to $CH_4$, $CO_2$ and $HCO_3^-$. The methane which can be used as fuel leaves the reactor 21 via the outlet 26. The process can be repeated by passing another batch of organic acid containing-liquid from the first reactor through the anion exchanger.

The bicarbonate solution used to desorb the organic acid anions may be introduced into the apparatus via inlet 22 and valve 23 or recycled from the second reactor 21 via pump 24, tubing 25 and valve 23.

Figure 2:
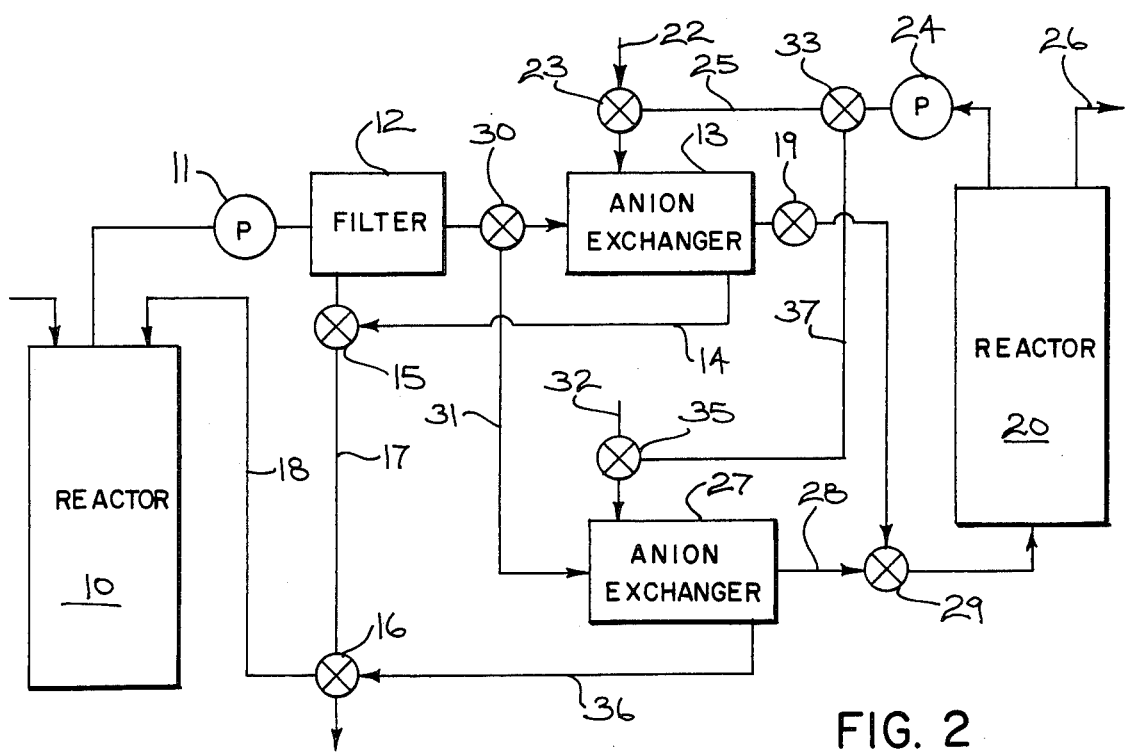

In FIG. 2 an apparatus for a continuous process is shown. It differs primarily from the apparatus of FIG. 1 in that there is a second anion exchanger 27 and additional pumps, valves and tubing connecting the second exchanger into the system.

In operation the second anion-exchanger 27 of the apparatus of FIG. 2 is initially loaded with organic acid anions and they are desorbed and the anion exchange material put back in the bicarbonate form by using filtered bicarbonate solution from the syntrophic methanogenic second reactor 21. The desorbed organic acid anions are transported from the anion exchanger 27 via tubing 28 and valve 29 into the second reactor 21 where the organic acids are converted to $CH_4$, $CO_2$ and $HCO_3^-$ (see Table 1). With proper timing the flow of the first reactor can be passed alternately through two anion exchangers 13 and 27 to provide a continuous process.

In the continuous process apparatus, the flow of filtrate from the filter 12 is controlled by the valve 30 which can be operated to direct flow to either the first exchanger 13 or the second exchanger 27 via tubing 31. Bicarbonate can be introduced into the exchanger 27 via the inlet 32 or directed to it from reactor 21 via tubing 25, 37 and valves 33 and 35. The organic acid free residue of the filtrate leaving exchanger 27 can be returned to the first reactor or removed from the system via tubing 36 and valve 16.

The second reactor 21 is preferably operated as an upflow reactor in order to retain the dense particulate syntrophic microorganisms in the reactor, but any type of reactor that can carry out reactions listed in Table 1 is suitable.

In both the apparatus of FIG. 1 and 2 the methane rich biogas from the second reactor 21 is collected via outlet 26.

The present invention possesses many advantages over the prior art processes and apparatus. The specially preferred continuous process and apparatus by providing process stage separation with the trophic group I biocatalysts, i.e. microorganisms, contained in the first hydrolysis reactor and the trophic groups II and III contained in the second syntrophic biomethanation reactor and, by introducing an anion-exchange substrate shuttle as the two stage and two reactor coupler the following advantages for process operation and stability are achieved:

(a) The novel ability to uncouple the volumetric flows of the hydrolysis and methanogenesis stage and by this to separately improve the dilution rates of both process stages. Thus, the required reactor sizes and implicitly the investment costs can be independently minimized for both waste treatment stages;

(b) The novel ability to constantly and selectively remove inhibitory fermentation acids from the first hydrolysis reactor. Thus the specific microbial conversion rates of the hydrolysis step improve due to the absence of end product inhibition;

(c) The novel ability to maintain the organic acid content of an effluent from a biomethanation process at very low concentrations by anion-exchange treatment and to provide high organic acid anion concentrations at essentially neutral pH to the second syntrophic biomethanation reactor. This allows operation under conditions where the trophic group II and III biocatalysts are fully substrate saturated which dramatically enhances the volumetric biomethanation rates but still allows the effluent from the overall process to be very low in organic acids.

(d) The novel ability to protect the very sensitive biocatalysts in trophic groups II and III from oxygen, neutral and slightly acidic toxins, antibiotics and other specifically inhibitory compounds, which are contained in the fluid from the first hydrolysis reactor and, which do not bind to the anion-exchange material. Examples for this are ammonium or monensin as an antibiotic. This provides higher process stability for the sensitive portion of the biomethanation ecosystem;

(e) The novel ability to design an optimal feed substrate for the second syntrophic biomethanation reactor comprised of organic acid anions from the first reactor but with low dilution or contamination from the fluid of the hydrolysis stage. Thus, addition of essential growth factors or metabolic cofactors and minerals for the syntrophic biomethanation of dilute or concentrated wastes could become economically feasible;

(f) The novel ability to constantly select within a waste treatment process for two separated but dense particulate biocatalysts, one optimized for organic hydrolysis to acids the other for the syntrophic biomethanation of organic acids. This allows the most economic use of the expensive reactor volume, as nonparticulate populations with lower volumetric reaction rates and growth rates would be constantly washed-out; and, two separate biocatylsts types are optimized for individual rate limiting steps; and, (g) The novel ability to produce a biogas with guaranteed methane contents of greater than 80% without any physical treatment or upgrading of the produced gas. In the case of an anionic-exchange substrate shuttle controlled process, methane contents of greater than 90% are achieved (see Table 2). This opens the way for high grade uses of the produced methane as a chemical feedstock or a natural gas substitute. The invention is further illustrated by the following examples:

EXAMPLE 1

Anion-exchange resin (55 g of Dowex 1X8) was poured into a glass column (5.5 cm diam.) and was converted to the bicarbonate-form at room temperature by passing 3.5l of 1 N NaOH, 3.5l of H$_2$O, 200 ml of 1M NaHCO$_3$ and 500 ml of 0.1M NaHCO$_3$ over the resin at a rate of 25 ml/min. To simulate the fermentation product of an acidogenic fermentation an aqueous solution containing 50 mM Na-acetate, 50 mM Na-propionate and 50 mM Na-butyrate at a pH of 5.5 was prepared and passed through the resin at a rate of 3 ml/min. The effluent was collected and analyzed. The pH of the effluent varied between 7.2 and 7.3 and the [HCO$_3^-$] between 50 and 80 mM. The organic acid (VFA) contents were analyzed by gas chromatography on Chromosorb 101 (Alltech. Inc.) after acidification with 1 N H$_3$PO$_4$. During most of the time only traces of the VFA appeared in the effluent. The exchanged bicarbonate buffered the acidic pH of the synthetic fermentation liquid, raised the pH of the effluent from 5.5 to 7.2 and contained excess bicarbonate (50-80 mM) for further buffering in the acidogenic hydrolysis process stage.

EXAMPLE 2

An anion-exchange column loaded with acetate, propionate and butyrate identical to Example 1, was pumped until liquid flow ceased and then eluted with an aqueous solution of 100 mM NaHCO$_3^-$ (pH=7.6) at a pump rate of 25 ml/min to simulate the fluid composition from a synthrophic biomethanation reactor. The effluent pH (7.05-7.4) was lower than the pH in the NaHCO$_3$ solution demonstrating the production of process acid during the anion exchange substrate shuttle process. Dissolved VFA's were analyzed as described in Example 1.

The dissolved VFA-anions concentrations reached approximately 75% of the theoretically possible value (100 mM total at 100 mM NaHCO$_3^-$). This demonstrates the rapid and quantitative nature of the desorption of VFA-anions from the resin by bicarbonate ions. The recovery of VFA from the anion-exchange resin was greater than 97%.

EXAMPLE 3

An upflow loop-reactor containing a 28 ml bed of a dense, particulate syntrophic organic anion biomethanation biocatalyst was fed at 35° C. with a mixture of 100 mM Na-acetate, 55.4 mM Na-propionate and 48.2 mM Na-butyrate dissolved in a medium of essential minerals, 0.05% (w/v) yeast extract and 5 mM sodium-phosphate at pH 4.5. The dilution rate was 0.1/h and no substrate shuttle unit was used. In steady state operation a pH-value in the effluent of 7.4 and a [HCO$_3^-$] of 90-100 mM was measured. The produced biogas had a methane content of 72%. The methane-productivity was under standard conditions (1 atm, 0° C.) 80-100 VCH$_4$/Vbed/d. The characteristic parameters of the VFA-conversion are shown in Table 3. The removal of VFA-anions was greater than 90% showing that this reactor had all the properties needed for the second reactor of an anion-exchange substrate shuttle process.

The [HCO$_3^-$] (100 mM) and the amount of CO$_2$ produced during steady state operation (100 mM) would be sufficient to provide the second reactor with concentrations up to 100 mM of VFA-anions via a substrate shuttle process (see Example 2).

EXAMPLE 4

An upflow loop-reactor identical to Example 3 with a basically identical medium composition was fed at different pH-values in shock loads with concentrations of all three VFA simultaneously above 10 mM and up to 50 mM to saturate the respective second reactor biocatalysts. The pH was adjusted by varying the dilution rate and adding neutral solutions of the sodium salts of the respective missing VFA-anion. Very high methane productivities up to 140 VCH$_4$/Vbed/d were recorded at each pH value for more than 1 h over a broad pH range between 6.6 and 7.6. This shows that the second reactor biocatalysts had considerable stability against VFA-overloading and pH variations. The very high methane-productivity further demonstrates the comparatively high VFA-removal capacity of the syntrophic organic acids biomethanation reactor.

Representative biocatalysts that can be employed include the following genera:

(a) Group I - hydrolytic fermentative bacteria such as Clostridium, Pseudomonas and Enterobacter;

(b) Group II - syntrophic H$_2$-producing bacteria such as Syntrophobacter, Syntrophomonas, Clostridium, and Desulphovibrio; and (c) Group III - methanogenic bacteria such as Methanobacterium, Methanosarcina and Methanothrix.

Those skilled in the art will be aware of the anion exchange materials that can be used. In general any anion exchange material that will adsorb the organic acid anions and allow the anions to be desorbed can be employed. Especially preferred are the anion exchangers that can be placed in the bicarbonate form to adsorb the anions and which allow the anions to be desorbed with bicarbonate.

TABLE 1

Balanced methanogenic conversions in the SBR reactor of major selected organic acid anions produced in the COHR reactor provided by the anion-exchange substrate shuttle component.

| reaction | gas composition (% methane) |
|---|---|
| acetate$^-$ + H$_2$O—CH$_4$ + HCO$_3^-$ | 100% |
| 4 propionate$^-$ + 6 H$_2$O—7 CH$_4$ + 4 HCO$_3^-$ + CO$_2$ | 87% |
| 2 butyrate$^-$ + 4 H$_2$O—5 CH$_4$ + 2 HCO$_3^-$ + CO$_2$ | 83% |
| 8 lactate$^-$ + 8 H$_2$O—12 CH$_4$ + 8 HCO$_3^-$ + 4 CO$_2$ | 75% |

TABLE 2

Predicted gas composition in the SBR reactor fed with typical organic acid mixtures produced in the COHR reactor.

| | gas composition (% methane) | |
|---|---|---|
| products as methanogenic substrates | with substrate shuttle unit | without substrate shuttle unit |
| homoacetate | 100% | 50-60% |
| acetate/butyrate (2:1) | 90% | 70-75% |
| acetate/propionate (1:1) | 91% | 70-75% |
| acetate/lactate (1:1) | 84% | 50-60% |
| homolactate | 75% | 50-60% |

TABLE 3

Organic acid anion removal by a syntrophic organic acids biomethanation reactor.

| organic anion | feed- (mMol/l) | effluent- (mMol/l) | conversion rate (Mol/l) | COD removal |
|---|---|---|---|---|
| acetate | 100.2 | 9.3 | 3.5 | 90% |
| propionate | 55.4 | 8.5 | .72 | 84% |
| butyrate | 48.2 | 0.1 | .72 | 99% |

It will be readily apparent to those skilled in the art that the bicarbonate solution and the organic acids preparations which are introduced into the anion exchanger to desorb the adsorbed organic acid anions and to desorb the bicarbonate ions, respectively, must be of sufficient pH to perform the desired functions with the selected anion exchange material. The bicarbonate solution may be an aqueous solution of an alkali, alkaline metal or ammonia salt and it will normally be equivalent to about 0.1 M sodium biocarbonate and have a pH of about 7.6. The organic acid anion containing liquid from the first reactor will normally have a pH of about 5 to about 6.5.

It also will be apparent to those skilled in the art that the first stage which produces the organic acids may be a biological or chemical treatment and in which the temperatures may range from about 1° C. to about 500° C. The second methanogenesis stage may be conducted from about 1° C. to about 99° C. and preferably at 30° C. to about 50° C. In addition, the pressures employed can be varied; however, a pressure of one atmosphere is preferred.

It further will be apparent that a number of additional changes and modifications may be made without departing from the spirit and scope of the present invention. Therefore, the invention should not be limited except by the claims.

I claim:

1. A process for the biomethanation of an organic substrate to methane which comprises: treating the substrate in a first reactor to form a liquid containing dissolved organic acid anions; adsorbing said anions on an anion exchange material; removing the organic acid anion-free residual liquid; desorbing the organic acid anions from the anion exchanger to obtain an aqueous organic acid anion containing preparation; and transporting said preparation to a second reactor containing methanogenic bacteria which consume the organic acid anions and produce methane.

2. The process of claim 1 in which the anion exchange material is in the bicarbonate form and bicarbonate solution is used to desorb the anions.

3. The process of claim 2 in which aqueous bicarbonate solution is produced in the second reactor and it is subsequently used to regenerate the anion exchange material to the bicarbonate form and to desorb the organic acid anions.

4. The process of claim 1 in which the substrate is hydrolyzed in the first reactor with hydrolytic microorganisms.

5. A biomethanation process comprising a first microbial hydrolysis stage and a second methanogenesis stage, said process comprising the following steps:

(a) hydrolyzing an organic substrate to form a solid phase and an organic acid anion-containing liquid phase, and separating the liquid phase;

(b) passing the liquid phase into contact with an anion exchange material provided in the bicarbonate form to adsorb the organic acid anions and to desorb the bicarbonate, and separating the resulting bicarbonate solution;

(c) regenerating said anion exchange material with a second bicarbonate solution which is of sufficient strength to effect the desorption and dissolution of said acid anions and the simultaneous adsorption of bicarbonate on the anion-exchange material;

(d) subjecting said desorbed acid anions to a methanogenesis stage to convert the organic acid anions into methane, carbon dioxide and bicarbonate by action of densely aggregated $H_2$-producing acetogenic bacteria and, $H_2$-consuming and acetate-cleaving methanogenic bacteria; and, (e) utilizing some of the bicarbonate produced in said methanogenesis stage as the second bicarbonate solution.

6. A process of claim 5, wherein the bicarbonate solution of step (b) is used to raise the pH of the hydrolysis stage.

7. A process of claim 5, wherein the solid phase from the separation step (a) is recycled to the hydrolysis stage.

8. A process of claim 5, wherein the anion-exchange material is converted in its bicarbonate form by treatment with an aqueous solution of a bicarbonate salt of alkali, alkaline earths or ammonia.

9. A process of claim 5, wherein the organic acid anion concentration in the methanogenic stage exceeds 10 mM.

10. A process of claim 5, wherein the two stages are conducted in independent reactors which do not have a common liquid phase connecting them so that said hydrolysis and methanogenesis stages can be eco-engineered to the individual pressure optima, the individual temperature optima, the individual pH-optima, individual optimum loading rates, individual aqueous medium composition and individual optimum nonaqueous medium composition or support materials of each of said process stages without interference from the other stage.

11. A process of claim 5, wherein a pressure of essentially 1 atm is employed and the methane composition of the untreated produced gas from the methanogenesis stage exceeds 80% methane due to the bicarbonate removal during regeneration of the anion exchange material.

* * * * *

UNITED STATES PATENT AND TRADEMARK OFFICE
CERTIFICATE OF CORRECTION

PATENT NO. : 4,781,836

DATED : November 1, 1988

INVENTOR(S) : Thiele et al.

It is certified that error appears in the above-identified patent and that said Letters Patent is hereby corrected as shown below:

Column 4, line 14    delete "solution"

Signed and Sealed this

Second Day of May, 1989

Attest:

DONALD J. QUIGG

*Attesting Officer*    *Commissioner of Patents and Trademarks*